US006586134B2

(12) United States Patent
Skoumpris

(10) Patent No.: US 6,586,134 B2
(45) Date of Patent: Jul. 1, 2003

(54) ELECTRODE LEAD TO CASE AND HEADER, LASER/ELECTRON BEAM WELDING

(75) Inventor: John Skoumpris, Amherst, NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 255 days.

(21) Appl. No.: 09/821,672

(22) Filed: Mar. 29, 2001

(65) Prior Publication Data

US 2002/0142216 A1 Oct. 3, 2002

(51) Int. Cl.[7] .......... H01M 2/06
(52) U.S. Cl. .......... 429/178; 429/181
(58) Field of Search .......... 429/65, 146, 175, 429/178, 179, 181, 237

(56) References Cited

U.S. PATENT DOCUMENTS 880,703 A 3/1908 Wheeler
1,971,275 A 8/1934 Rock
3,969,142 A 7/1976 Greatbatch et al. .......... 136/83
4,394,059 A 7/1983 Reynolds .......... 339/125
4,663,248 A 5/1987 Klein et al. .......... 429/169
4,873,160 A 10/1989 Miyazaki et al. .......... 429/170
5,955,217 A 9/1999 Van Lerberghe .......... 429/162

*Primary Examiner*—Randy Gulakowski
*Assistant Examiner*—Monique Wills
(74) *Attorney, Agent, or Firm*—Michael F. Scalise

(57) ABSTRACT

The present invention provides a new process for attaching the anode lead to the battery case, creating a case negative design. The anode lead is an extension of the anode current collector and is nested between the case and the lid. Excess lead material is ground or cut off and the case to lid seal is achieved by laser/electron beam welding. The new procedure enhances the hermicity of the cell and the new process is applicable to a number of additional applications. This includes primary lithium batteries, implantable batteries, lithium based rechargeable cells, also acid or alkaline based batteries.

13 Claims, 9 Drawing Sheets

20 62 57 54 49 4 61 66 63 21 19 72 64 46 47 22 25 10 43 4 41

20
57
62
61
21
66
63
64
54
19
72
60
59
47
49
46
48
23
53
27
55
22
25
10
43
41

ELECTRODE LEAD TO CASE AND HEADER, LASER/ELECTRON BEAM WELDING

BACKGROUND OF THE INVENTION

1. Field of the Invention

The present invention relates to the art of electrochemical cells, and more particularly, a novel anode electrical lead. Moreover, the current invention provides an electrical path for an implantable battery by positioning the anode lead between the battery case and the lid and welding the battery lid to the case creating a hermetically sealed battery. The new process is simpler, requiring fewer steps and saves manufacturing costs.

2. Prior Art

The recent rapid development in small-sized electronic devices having various shape and size requirements requires comparably small-sized electrochemical cells of different designs that can be easily manufactured and used in these electronic devices. Preferably the electrochemical cell has a high energy density, and one commonly used cell configuration is a prismatic, case-negative cell design having an intermediate cathode flanked by opposed anode plates in contact with the casing and in electrical association with the cathode. In conjunction with smaller size batteries, enhanced characteristics such as nesting a lead from the anode collector between the wall of the battery case and the lid, creating a battery case negative design, is a unique novel way to increase the applicability of these cells to a larger number of situations. The prior art does not disclose such a connection.

For example, turning now to the prior art patents, U.S. Pat. No. 4,663,248 to Klein et al. discloses a cell having spirally wound electrodes in which an extension of one of the electrodes is caught and compressively held between the inwardly curled end of the container wall. The patent specifies that the invention requires the container end be curled inwardly to effect the requisite terminal connection. This is not the case in the current development.

Also, U.S. Pat. No. 4,873,160 to Miyazaki et al. discloses a battery with a lead captured between the case and the cover plate. However, the case is of insulating material unlike the cell of the current development.

Again, U.S. Pat. No. 1,971,275 to Rock discloses a negative battery terminal strip soldered to the zinc can below the upper end of the battery. The strip has a portion is connected to the terminal post. The lead external to the battery casing diminishes the applicability of the invention to various situations, in contrast to the invention which is disclosed in this application which increases the applicability of battery designs heretofore unrealized.

Finally, U.S. Pat. No. 5,955,217 to Van Lerberghe discloses a flat battery in which electrodes have portions extending between a cover foil and conductive frame parts. In this invention, there is no disclosure of removing excess lead or any welding, which is contrary to the teachings of the current invention. These untrimmed extensions and the like create cumbersome arrangements which are hard to use in various applications.

Thus, it can be seen, based on the disclosed prior art, that there is a need to develop a new anode electrode termination which will extend the applicability of the current electrochemical cells to new varieties of applications. The current invention advances technology and reduces manufacturing costs and fills many of the needs hereinbefore left unfilled.

SUMMARY OF THE INVENTION

The present invention provides a new battery design for attaching at least one anode lead to a battery case, creating a case negative design. The anode lead is nested between the case and the lid and the excess lead above the surface of the lid is ground or cut off and the case to lid seal is achieved by laser/electron beam welding. The new procedure enhances the hermicity of the cell and the new process is applicable to a number of additional applications. These include primary lithium batteries, implantable batteries, lithium based rechargeable cells, and also acid or alkaline based batteries.

The foregoing and additional advantages and characterizing features of the present invention will become clearly apparent upon a reading of the following detailed description together with the included drawings.

BEST MODE FOR CARRYING OUT THE INVENTION

Referring now to FIGS. 1 through 4, electrochemical cell 10 is similar to the prismatic electrochemical cell as described in U.S. Pat. No. 5,250,373 to Muffoletto et al. This patent is assigned to the assignee of the current invention and the disclosure of which is incorporated herein by reference.

Figure 1:
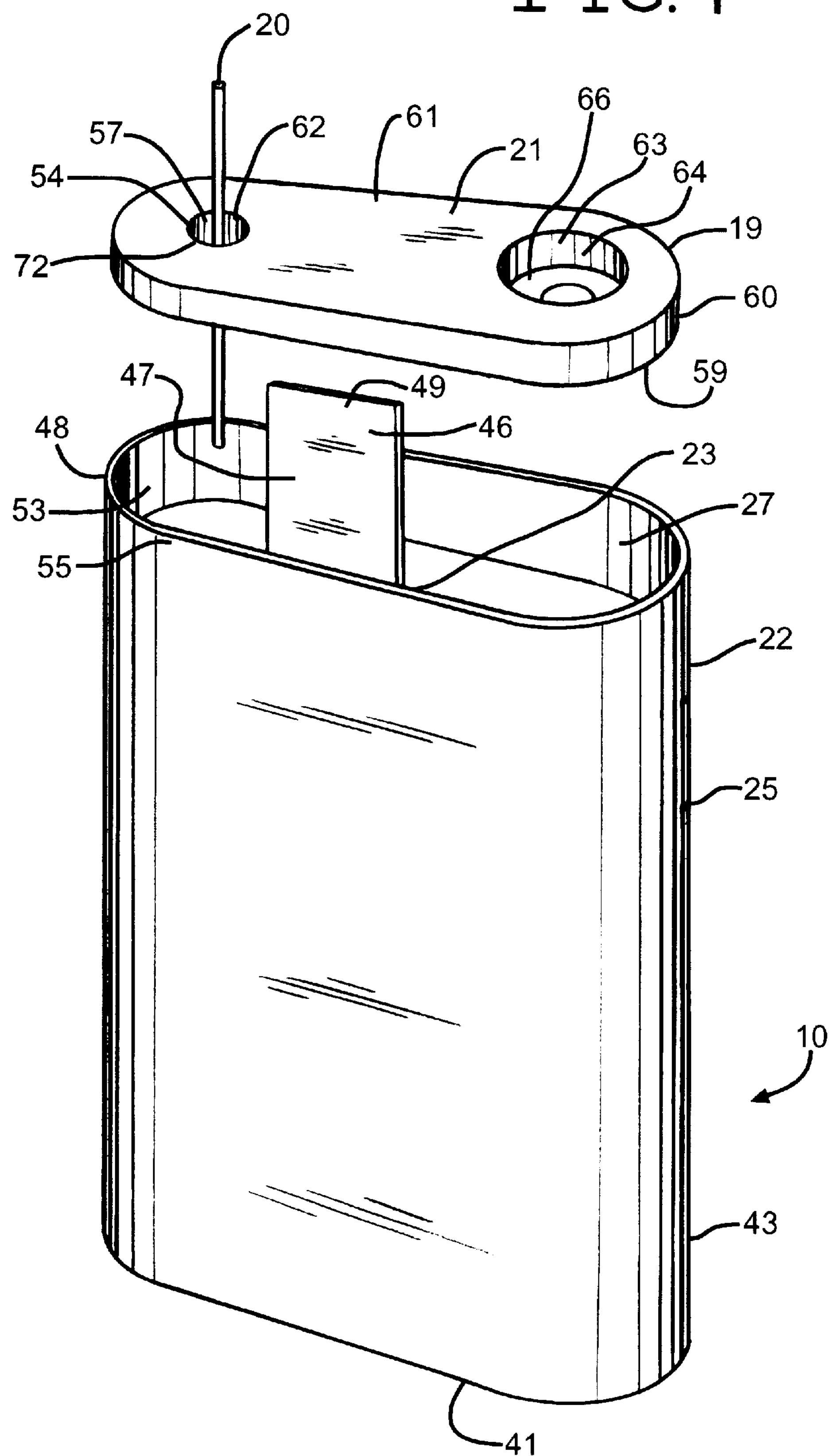
FIG. 1 is a perspective view of an electrochemical cell in the open position showing the anode lead attached to the current collector.
Figure 2:
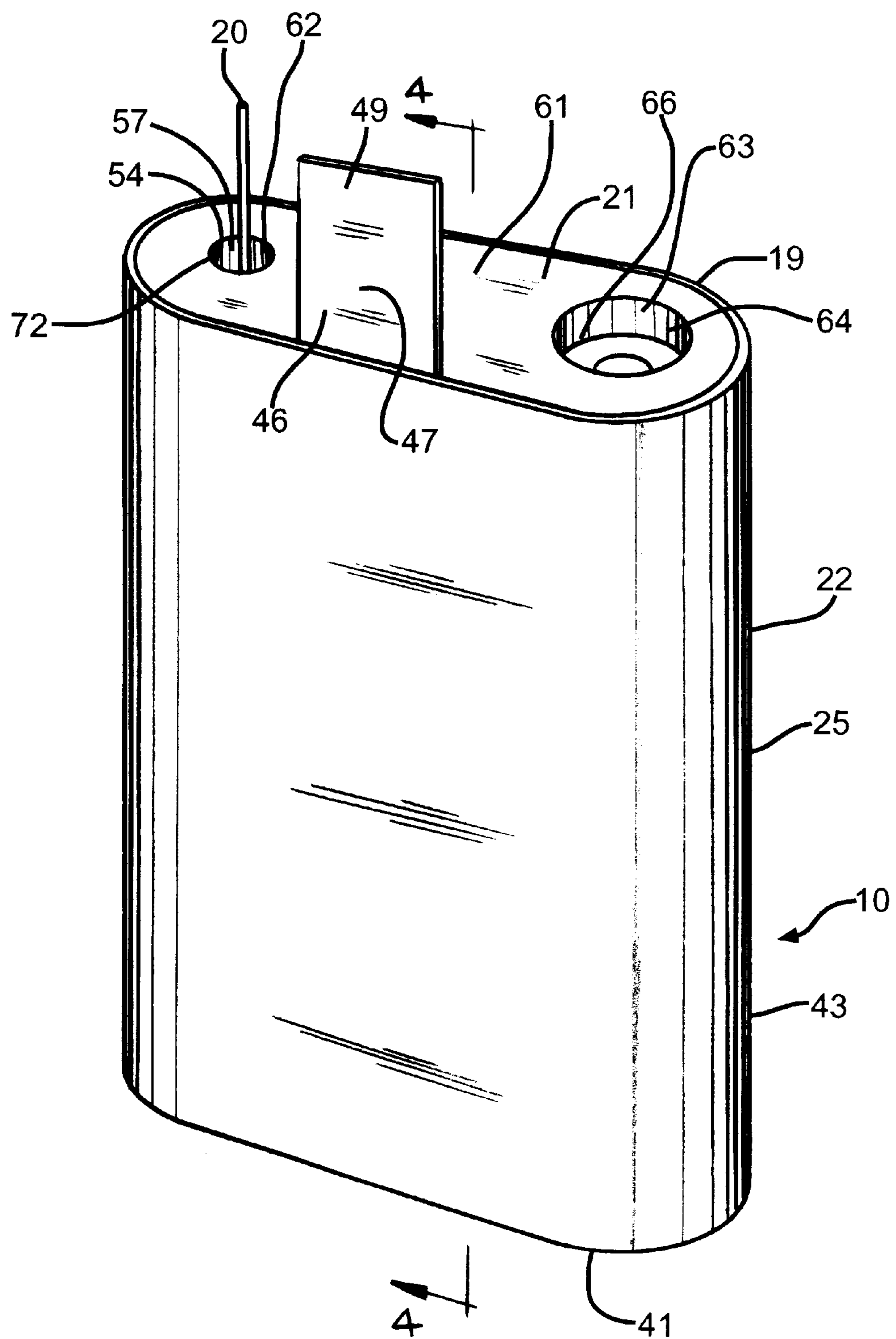
FIG. 2 is a perspective view of the battery case in the closed position, with excess anode lead extending above the top of the case.
Figure 3:
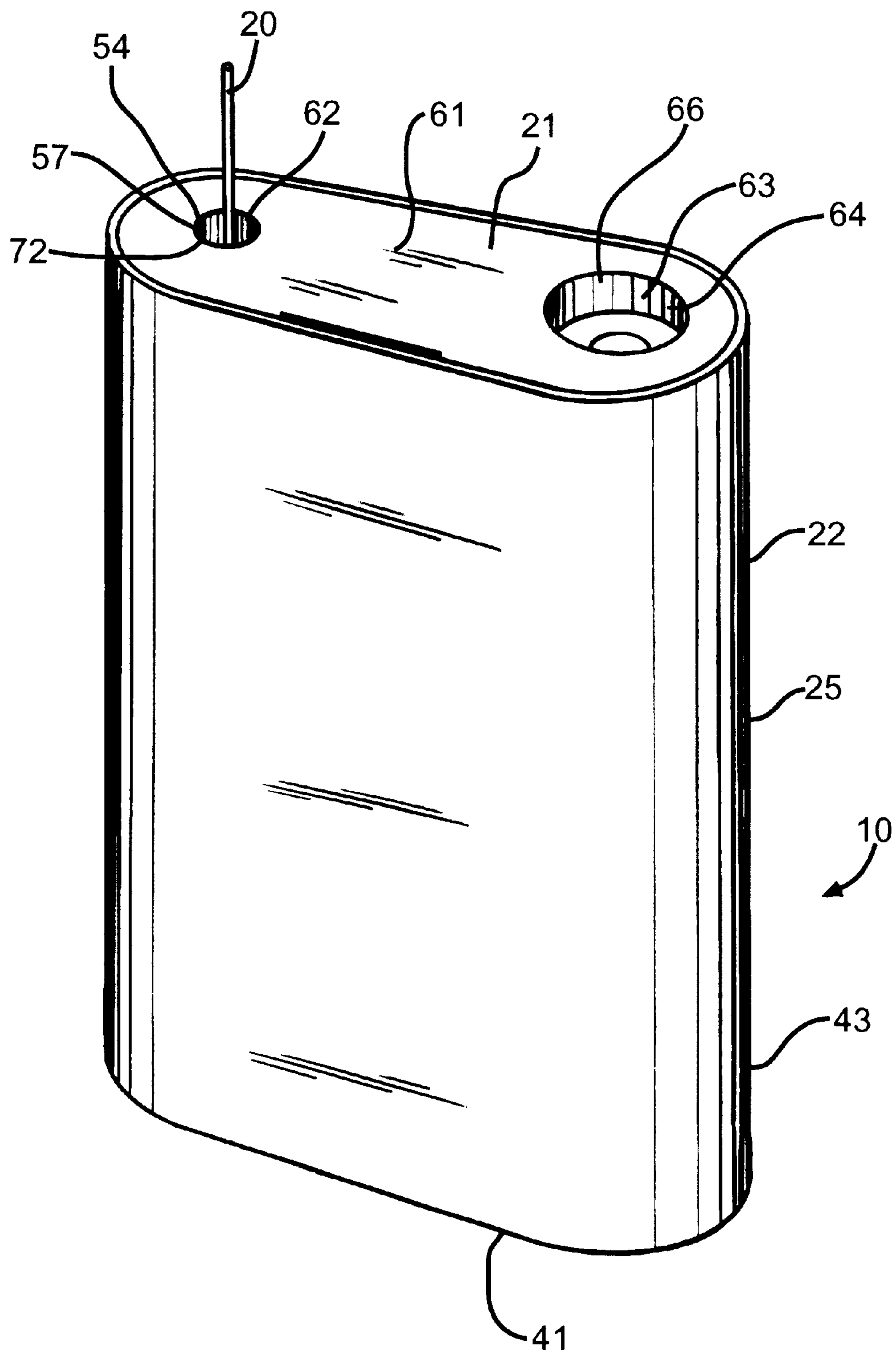
FIG. 3 is a perspective view of the battery case in the closed position with the excess anode lead removed prior to welding.

Battery casing 22 in this embodiment consists of two parts, a first part or body 25 and a second part or lid 21 as shown in FIGS. 1 through 3. The lid 21 is received inside the opening 27 of the body 25 and welded to provide a hermetic enclosure for an electrode assembly 23. The preferred methods of sealing the casing are welding and brazing. Casing 22 is of a conductive material preferably selected from the group consisting of nickel, aluminum, stainless steel, mild steel and titanium. An external cell electrical connection is provided by the terminal lead 20 and by a contact region comprising the entire conductive casing 22, which is insulated from the terminal lead 20, to prevent shorting.

Now, in particular, the body 25 comprises an ellipsoidal base wall 41, having a continuous side wall 43 extending to a continuous upper edge 48 defining an opening 27 of the body 25 opposite to the base wall 41. Side wall 43 has inner and outer surfaces 53 and 55.

Figure 7A:
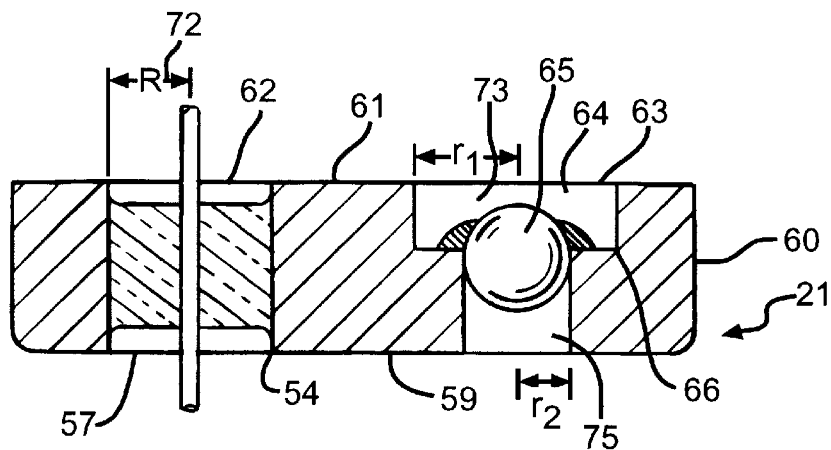
FIG. 7A depicts the first embodiment of the seal closure for the fill port.
Figure 7B:
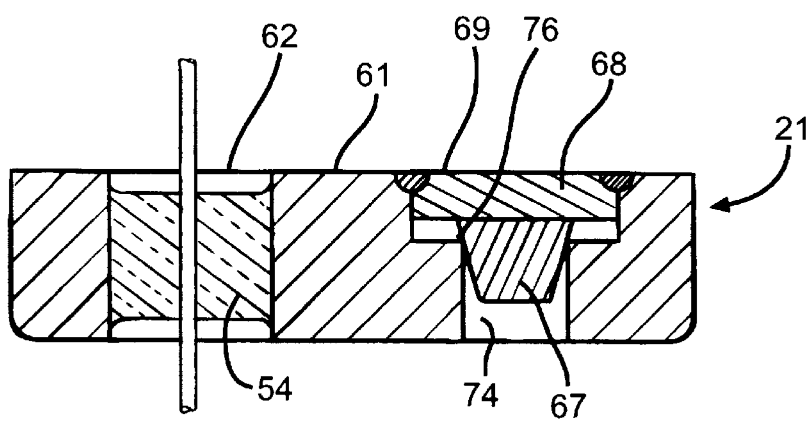
FIG. 7B depicts the second embodiment of the seal closure for the fill port.
Figure 7C:
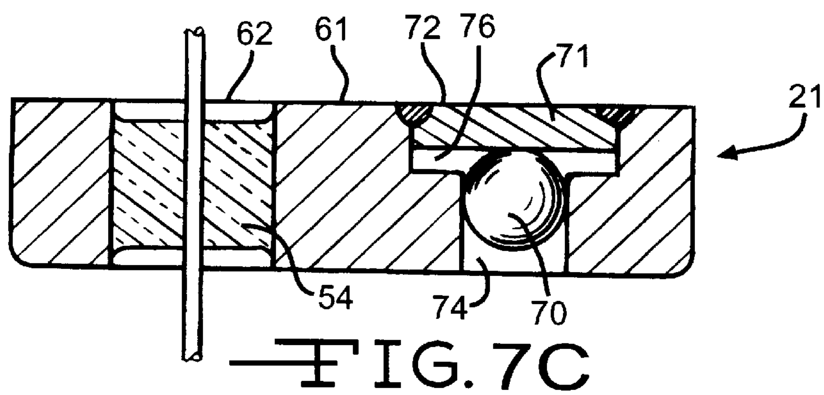
FIG. 7C depicts the third embodiment of the seal closure for the fill port.

The lid 21 is a one piece member, having an ellipsoidal shaped lower surface 59, with continuous side wall 60 extending to an upper surface 61. The lid 21 is sized to fit in a closely spaced relationship within the upper opening 27 in the body 25 of the case 22. The lid 21 is provided with first and second openings 62 and 63. The first opening 62 is used for a hermetically sealed battery terminal feed through 57, containing a glass-to-metal seal 54 whereas the second opening 63 is used for an electrolyte fill opening 64. As shown in FIGS. 7A through 7C, the first opening 62 of the lid 21, is further defined by a continuous cylindrical opening of fixed radius 72. In that respect, the opening 62 extends downwardly from the upper surface 61 and meets with lower surface 59.

The second opening 63 is further defined by a discontinuous cylindrical aperture of fixed radius $r_1$ 73 extending downwardly from the top surface 61 to a point approximately midway between the top 61 and bottom surface 59 where the opening passes through a transition 66 to a cylindrical opening of radius $r_2$ 75 (where $r_1>r_2$) extending further downward and meeting with the lower surface 59. The first and second openings 62 and 63 are co-axial. After filling the casing with electrolyte 56, a closure member may be sealed therein by welding. The closure mechanism will be described in detail later.

Figure 4:
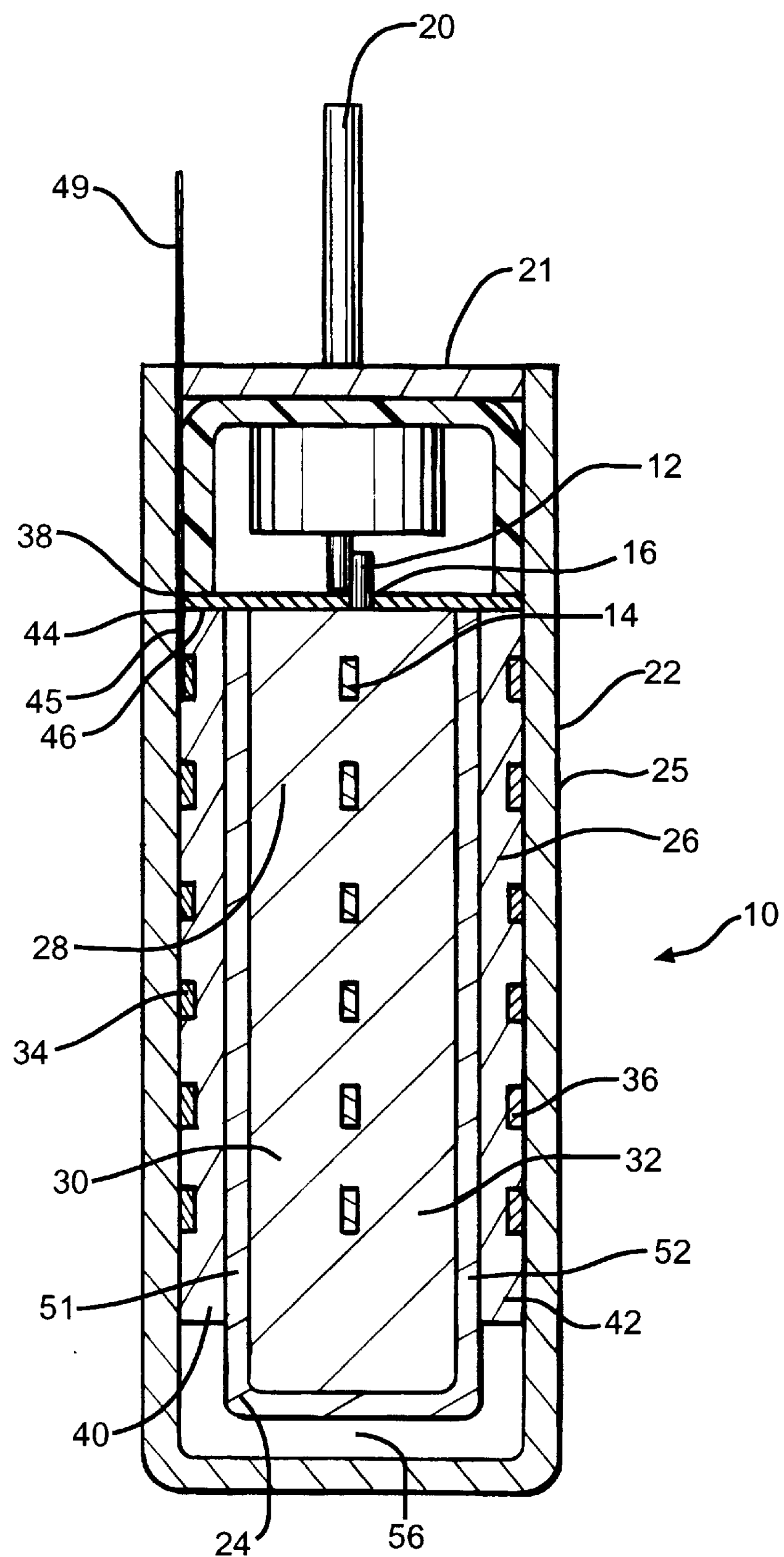
FIG. 4 is a section view along line 4—4 of FIG. 2.

As shown in FIG. 4, the cell further includes anode and cathode electrodes. The cathode 28 includes current collector 12. Cathode collector 12 is a unitary member generally comprising a grid 14 connected to a connection tab 16. A terminal lead 20 is directly contacted to the tab 16 of the current collector 12, preferably by welding, to provide for direct electrical connection to the cathode electrode. The current collector 12 is readily incorporated into alkali metal/solid cathode or alkali metal/oxyhalide electrochemical cells of both solid cathode and liquid electrolyte types without having to be changed or otherwise modified. In the primary solid cathode type, for example a lithium-solid cathode cell, a solid cathode material such as silver vanadium oxide or copper silver vanadium oxide is contained within casing 22 and surrounded by a separator 24. However, the solid cathode material is not limited to silver or copper vanadium oxide, or copper silver vanadium oxide, but can also be manganese dioxide, or an oxide of cobalt, nickel or copper or a sulfide of copper, iron, titanium, or mixtures thereof. A lithium anode 26 also is in the casing.

In the liquid cathode/electrolyte or catholyte type cell, for example a lithium-oxyhalide cell, liquid catholyte fills the casing interior and is in operative contact with the anode and with the cathode element comprising the cathode current collector 12 according to the present invention sandwiched between opposed carbonaceous plates. A separator 25 is disposed between the anode and the carbonaceous cathode. For a more detailed description of such a liquid electrolyte cell references may be made to U.S. Pat. No. 4,246,327 to Skarstad et al., which is assigned to the assignee of the present invention, the disclosure of which is hereby incorporated by reference.

Referring now to FIG. 4, the cell 10 according to this embodiment of the present invention is of the liquid electrolyte type comprising a cathode electrode having a body 28 of solid cathode material in the form of plates 30, 32 pressed together and bonded against the cathode current collector 12. As previously stated, the cathode active material is preferably comprised of a metal, a metal oxide, a mixed metal oxide or a metal sulfide; and the cathode current collector 12 is fabricated from a thin sheet of metal selected from the group consisting of nickel, aluminum, stainless steel, mild steel and titanium, with titanium being preferred.

Now, as further shown in FIG. 4, cell 10 includes an alkali metal anode electrode, generally designated 26, comprising a unitary, conductive member which serves as the anode current collector and is fabricated from a thin sheet of metal, preferably nickel, having a pair of wing-like sections 34 and 36 joined by an intermediate web section 38. The preferred alkali metal for the anode is lithium. Lithium anode elements 40 and 42 are in pressure bonded contact with and carried by corresponding ones of the electrode wing sections 34 and 36, respectively. The wing-like sections 34 and 36 are of mesh formation to facilitate adherence to the lithium anode elements 40, 42. The lithium anode elements 40 and 42 are of similar shape or configuration as the corresponding electrode wing sections 34 and 36, respectively, but of a slightly larger size or surface area so as to define a marginal or peripheral extension or border surrounding the perimeter of each wing section. Thus, the length and width of each of the lithium anode elements 40 and 42 are slightly greater than the length and width of the corresponding electrode wing sections 34 and 36 with the anode elements terminating at an edge 44 a short distance from electrode web section 38.

Figure 5:
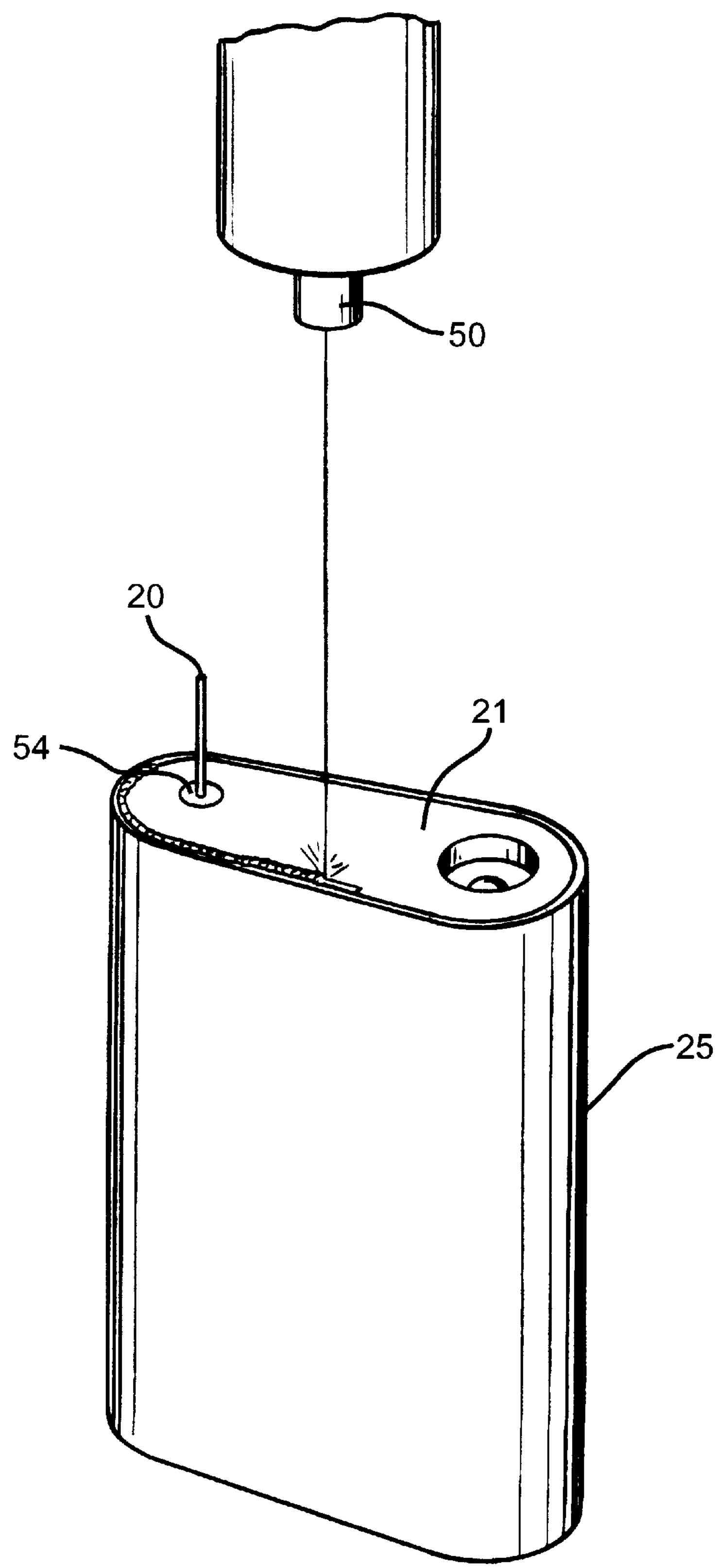
FIG. 5 shows sealing of the battery lid to the case by welding.

As further shown in FIG. 4, the anode lead 46 has first and second ends 45 and 49; the first end 45 is attached to the anode electrode section 38 in the vicinity of the wall 43 of the body 25 of the battery case 22. The anode lead 46 is of sufficient length that the second end 49 extends above the upper edge 48 of the casing body 25. The lid 21 is fitted to the casing body 25 nesting the anode lead 46 between the edge of the lid 19 and the inner wall surface 23 of the body 25. Once the lid 21 and the lower portion 25 are mated, the excess lead 47 of the second end 49 is trimmed by cutting or grinding and battery case 22 is sealed by welding using a laser/electron beam welding source 50 (FIG. 5) creating a hermetically sealed weld between the casing body 25 and lid 21. The lead 46 can be strap shaped, hexagonal and other geometric shapes. As one who is skilled in the art can realize that a multitude of different shapes can be used. However, it must be configured to be nested between the lid 21 and casing body 25.

To construct an anode-cathode subassembly according to the present invention, the electrode wing sections 34, 36 with the associated anode lithium elements 40, 42 are folded relative to web section 38 and toward each other and in a manner to place the lithium anode elements 40, 42 in operative contact with the oppositely directed surfaces 30 and 32 of the cathode body 28. In particular, lithium anode element 40 is in operative contact with the cathode body surface 30 through a thin sheet of separator material 51. Similarly, lithium anode element 42 is in operative contact with cathode body surface 32 through a thin sheet of separator material 52 such that separator sheets 51 and 52 surround and envelope the cathode body 28 to prevent direct physical contact with the anode plates 40, 42. Shielding and insulating sheets (not shown) are also provided between the web section 38 of the anode current collector and the cathode electrode 28. The terminal lead 20 connected to the current collector 12 of the cathode electrode 28 extends through a header assembly comprising the glass-to-metal seal 54 fitted in the lid 21.

As shown in FIG. 4, cell 10 is completed by a liquid electrolyte 56 provided in casing 10 and sealed therein by the provision of the closure means sealed to hermetically close the cell 10. Lead 20 is the positive electrical terminal, being connected to the cathode body 28. With anode electrode 26 being in operative contact with the conducting casing 22 through the anode lead 46 of the anode current collector affixed between the case wall and the lid by welding, the cell 10 of this embodiment of the present invention is in a case-negative electrical configuration.

As previously stated, the lead may be used in either primary or secondary electrochemical cells. The primary cells have hereinbefore been described. Now in the secondary electrochemical cell, the anode or negative electrode comprises an anode material capable of intercalating and de-intercalating the anode active material, such as the preferred alkali metal lithium. A carbonaceous negative electrode comprising any of the various forms of carbon (e.g., coke, graphite, acetylene black, carbon black, glass carbon, "hairy carbon" etc.) which are capable of reversibly retaining the lithium species is preferred for the anode material. A "hairy carbon" material is particularly preferred due to its relatively high lithium-retention capacity. "Hairy carbon" is a material described in U.S. Pat. No. 5,443,928 to Takeuchi et al., which is assigned to the assignee of the present invention and incorporated herein by reference. Graphite is another preferred material. Regardless of the form of the carbon, fibers of the carbonaceous material are particularly advantageous because they have excellent mechanical properties which permit them to be fabricated into rigid electrodes that are capable of withstanding degradation during repeated charge/discharge cycling. Moreover, the high surface area of carbon fibers allows for rapid charge/discharge rates.

Also in secondary systems, the positive electrode preferably comprises a lithiated material that is stable in air and readily handled. Examples of such air-stable lithiated cathode active materials include oxides, sulfides, selenides, and tellurides of such metals as vanadium, titanium, chromium, copper, molybdenum, niobium, iron, nickel, cobalt and manganese. The more preferred oxides include $LiNiO_2$, $LiMn_2O_4$, $LiCoO_2$, $LiCo_{0.92}Sn_{0.08}O_2$ and $LiCo_{1-x}Ni_xO_2$.

An electrolyte may also be required to activate the anode/cathode combination in the secondary system. The composition of the electrolyte will depend on the materials of construction of the anode and the cathode as well as the product application for the cell.

Figure 6:
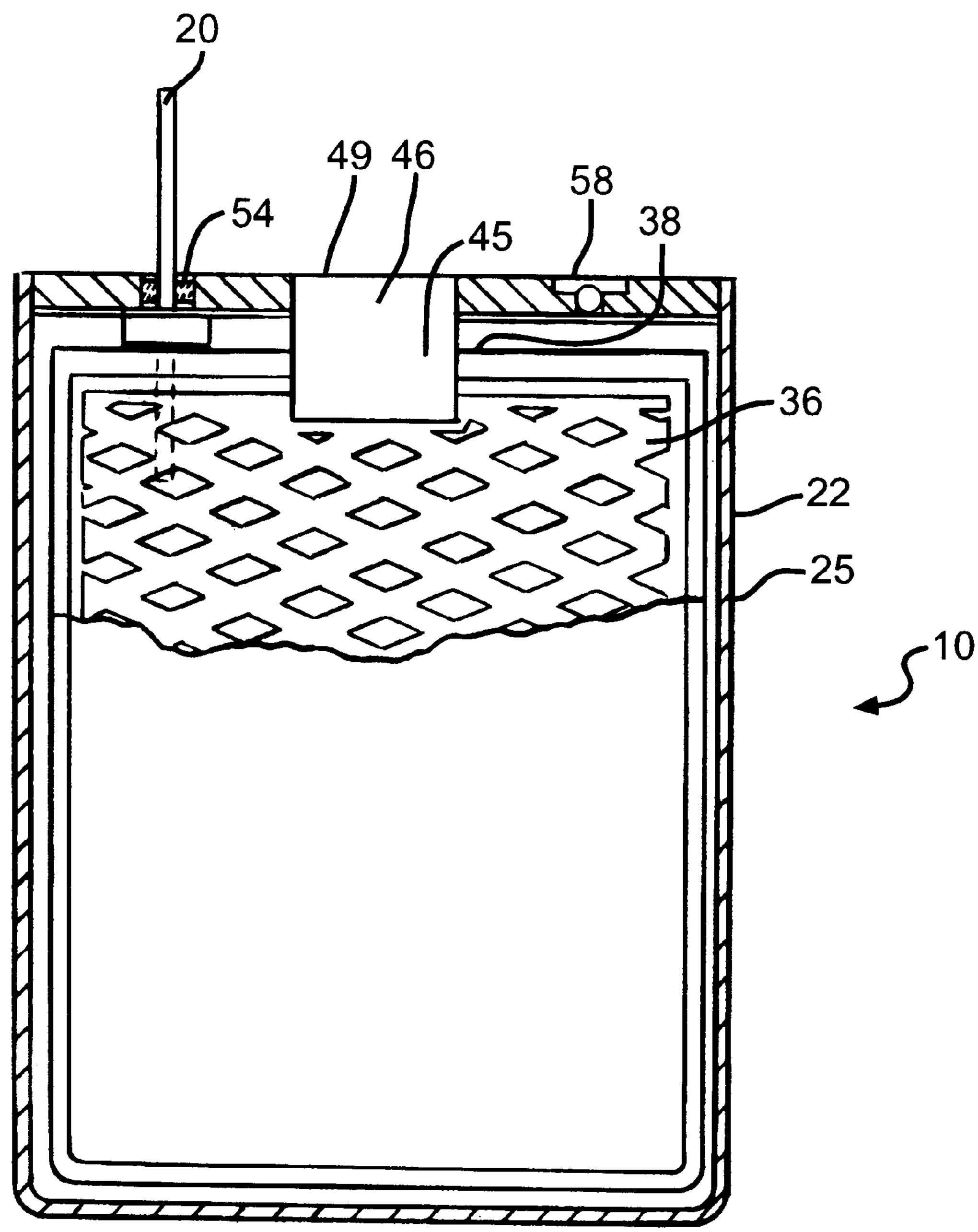
FIG. 6 is a perspective view with parts broken away of the anode current collector with anode lead attached prior to sealing of the battery lid by welding.

Leakage of electrolyte and gases from an electrochemical cell caused by a compromised seal is extremely undesirable and can even be fatal when the cell is used as the power source for an implantable medical device and the like. In electrochemical cells having a metal casing, one means of providing a hermetic seal, as previously stated, for an electrolyte fill opening and the like, is by welding a seal member 58 (FIG. 6) in the electrolyte fill opening 64. However, the casing proximate to the weld conducts heat to the electrolyte contained therein and some electrolyte evaporation invariably occurs. When these gases escape from the cell casing they are referred to as out gassed by-products and such escaping gases leave pin holes in the weld thereby compromising hermeticity.

Thus, in the current invention, several embodiments of the seal 58 may be effective to close the fill aperture 64 and assist to prevent comprising seals. In the first embodiment, a metal sealing member 65 in the shape of a ball is inserted in the second opening 63 (FIG. 7A). The member is flush with or slightly lower than upper surface 61 and is force fit into the sealing registry of the electrolyte fill opening 64 to form a secondary seal at the contact perimeter. Then, the primary seal is formed by welding the round metal member 65 to the transition 66 about the midpoint of the fill aperture 64.

In the second embodiment of the closure, a metal sealing member 67 (FIG. 7B) is fit into the lower portion of the fill aperture 64, surrounded by cylindrical opening 74. A second layer sealing disc 68 is installed in the upper aperture 76 slightly smaller than $2r_1$, where $r_1$ is the radius 73 of the upper portion 76 of opening 63, wherein the outwardly facing portion 69 of the second sealing disc 68 is flush or slightly recessed with the side wall surrounding the fill opening. The disc 68 is then welded to the upper surface 61 of the lid 21.

In the third embodiment of the closure, a metal sealing member 70 in the shape of a ball (FIG. 7C) is fit into the lower portion of the fill aperture 64, surrounded by cylindrical opening 74. A second layer sealing disc 71 is installed in the upper aperture 76 slightly smaller than $2r_1$, where $r_1$ is the radius 72 of the upper portion 76 of opening 63, wherein the outwardly facing portion 72 of the second sealing disc 71 is flush or slightly recessed with the side wall surrounding the fill opening. The disc 71 is then sealed to the upper surface 61 of the lid 21.

By way of example, in an illustrative cell, the active material of cathode body 28 is a silver vanadium oxide cathode material as described in U.S. Pat. Nos. 4,310,609 and 4,391,729 to Liang et al., or copper silver vanadium oxide as described in U.S. Pat. Nos. 5,472,810 and 5,516,340 to Takeuchi et al., all assigned to the assignee of the present invention, the disclosures of which are hereby incorporated by reference. Cathode current collector 12 is of titanium and terminal lead 20 is of molybdenum, separators 50, 51 are of polypropylene, electrolyte 56 is a 1.0M to 1.4M solution of $LiAsF_6$ or $LiPF_6$ in a 50:50 mixture of, by volume, 1,2-dimethoxyethane and propylene carbonate, glass seal 54 is of TA-23 Hermetic sealing glass, and closure means (not shown) is of stainless steel.

The current collector 12 of the present invention can also be employed in a cell having a case-positive electrical configuration. In particular, in the embodiments of FIGS. 1 thru 4, with the lithium anode elements 40, 42 contacting the conductive cell casing 22 through the anode lead 46, the cell 10 is in a case-negative electrical configuration. In a similar manner, a case-positive electrical configuration is provided by placing the cathode parts in contact with the conductive cell casing 22. In particular, and referring to the anode-cathode subassembly of FIG. 4, a case-positive electrical configuration is provided by replacing lithium anode elements 40, 42 with cathode plates 30, 32 on the electrode wing sections 34, 36. Accordingly, cathode body 28 would be replaced by a pair of lithium anode elements 40, 42 sandwiched together and against the current collector 12 of the present invention serving as an anode current collector which, in turn, is connected to the terminal lead 20 and insulated from lid 21 by the glass-to-metal seal 54. With the cathode parts in contact with electrode wing sections 34, 36 and with the electrode web section 38 in contact with the cell casing 22, a cell is provided in a case-positive electrical configuration. In all other respects, the anode current collector in the case-positive configuration is similar to that previously described with respect to cell 10 having the case-negative configuration.

In the current invention, the novel anode electrical lead has been discussed in conjunction with a prismatic casing having a bottom case and an upper lid or cover. However, this is for illustrative purposes only. As those who are skilled in the art can realize, the novel anode electrical lead is useful with any casing design which allows access to the external or internal surface of the anode lead, depending on the design needed. The available designs include clam shell, prismatic, cylindrical, or button shapes.

Figure 8A:
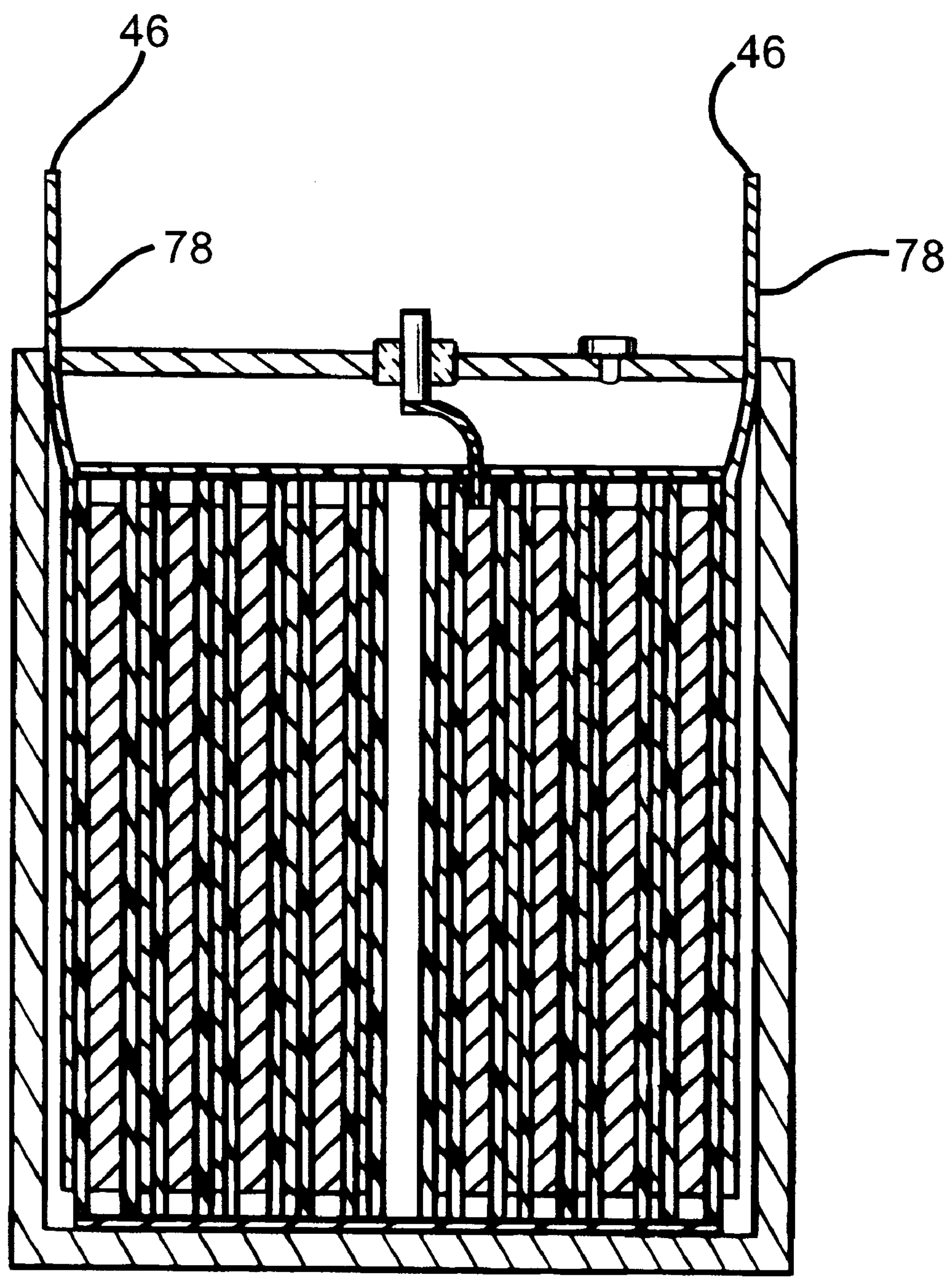
FIG. 8A is a perspective view of the jelly roll configuration with an electrode lead 46 for either extending through the lid.
Figure 8B:
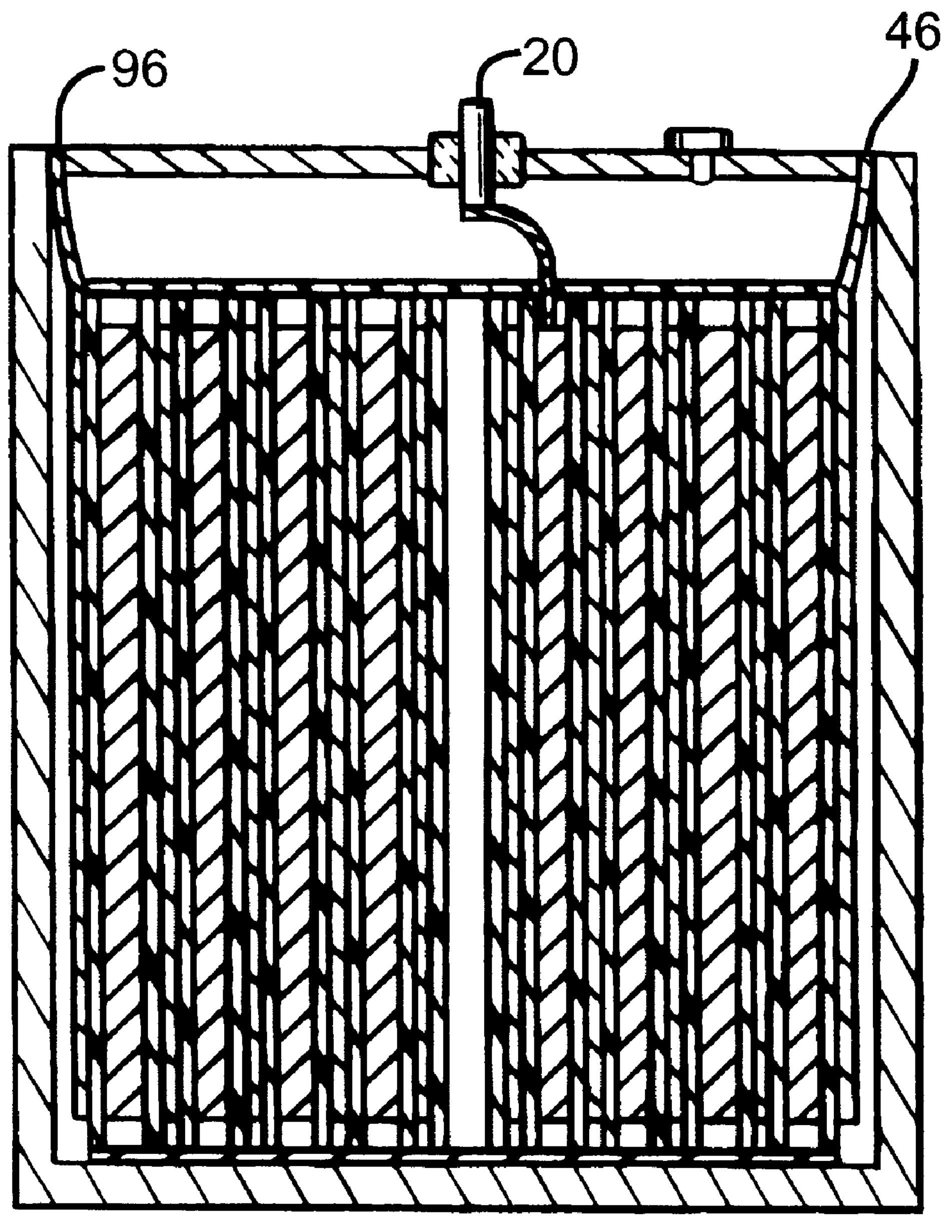
FIG. 8B is a perspective view of the jelly roll configuration with excess electrodes removed.

For example, FIGS. 8A and 8B show another embodiment of the present invention having the electrode lead 46 associated with a jellyroll electrode assembly. As previously described, the electrode lead 46 can be directly connected to either the anode electrode or the cathode electrode via their respective current collectors. In any event, the electrode lead 46 is first captured between the casing body 25 and the lid 21 with an extension portion extending above the lid. The extension portion 78 is removed and the lid is hermetically sealed to the casing body 25 in a manner as previously described (FIG. 8B).

The present invention may also be used with a number of different types of batteries including primary and secondary lithium batteries, and implantable batteries including those associated with implantable medical devices. It may also be used with acid or alkaline based batteries.

Now, it is therefore apparent that the present invention accomplishes its intended objects. While embodiments of the present invention have been described in detail, which is for the purpose of illustration, not limitation.

What is claimed is:

1. An electrochemical cell comprising a) a casing of an electrically conductive material and having an open end;

b) a first electrode comprising a first electrode active material contacted to a first current collector;

c) a second electrode comprising a second electrode active material contacted to a second current collector;

d) a terminal lead insulated from the casing and connected to one of the first and second current collectors;

e) a conductive extension connected to the other of the first and second current collectors;

f) an electrolyte activating the first and second electrodes; and g) a lid of an electrically conductive material closing the open end of the casing, wherein the conductive extension is trapped between the lid and the casing, and the lid is sealed to the casing to close the open end thereof.

2. The electrochemical cell of claim 1 wherein the conductive extension is flush with the lid sealed to the casing.

3. The electrochemical cell of claim 1 wherein the conductive extension is a plate-shaped member or a cylindrical-shaped member.

4. The electrochemical cell of claim 1 wherein the conductive extension is at least one selected from the group consisting of strap, triangular and hexagonal shapes.

5. The electrochemical cell of claim 1 wherein the first and second electrodes are electrically associated with each other in either a jellyroll configuration or in a prismatic configuration.

6. The electrochemical cell of claim 1 wherein the casing is selected from the group consisting of clam shell, prismatic, cylindrical and button casings.

7. The electrochemical cell of claim 1 wherein the casing, lid and conductive extension are of at least one selected from the group consisting of stain less steel, nickel, titanium and aluminum.

8. The electrochemical cell according to claim 1, wherein the lid and the casing containing the conductive extension are sealed by welding using a laser beam.

9. The electrochemical cell according to claim 1 wherein the lid and the casing containing the conductive extension are sealed by welding using an electron beam welder.

10. The electrochemical cell of claim 1 as a primary cell and the cathode active material is selected from the group consisting of silver vanadium oxide, copper silver vanadium oxide, manganese dioxide, cobalt oxide, nickel oxide, copper oxide, copper sulfide, iron sulfide, iron disulfide, titanium disulfide, copper vanadium oxide, and mixtures thereof.

11. The electrochemical cell of claim 1 as a secondary cell and the cathode active material is selected from the group consisting of oxides, sulfides, selenides, and tellurides of metals selected from the group consisting of vanadium, titanium, chromium, copper, molybdenum, niobium, iron, nickel, cobalt and manganese.

12. The electrochemical cell of claim 1 as a secondary cell and the anode material is selected from the group consisting of coke, graphite, acetylene black, carbon black, glassy carbon, hairy carbon, and mixtures thereof.

13. The electrochemical cell of claim 1 associated with an implantable medical device powered by the cell.

* * * * *